(12) United States Patent
DiGiovanni et al.

(10) Patent No.: US 9,395,242 B2
(45) Date of Patent: Jul. 19, 2016

(54) BROADBAND FIBER SENSOR ARRAY

(71) Applicant: OFS Fitel, LLC, Norcross, GA (US)

(72) Inventors: David J DiGiovanni, Mountain Lakes, NJ (US); Mikhail Sumetsky, Bridgewater, NJ (US)

(73) Assignee: OFS FITEL, LLC, Norcross, GA (US)

( * ) Notice: Subject to any disclaimer, the term of this patent is extended or adjusted under 35 U.S.C. 154(b) by 31 days.

(21) Appl. No.: 14/349,233

(22) PCT Filed: Oct. 6, 2012

(86) PCT No.: PCT/US2012/059149
§ 371 (c)(1),
(2) Date: Apr. 2, 2014

(87) PCT Pub. No.: WO2013/052932
PCT Pub. Date: Apr. 11, 2013

(65) Prior Publication Data
US 2014/0247453 A1    Sep. 4, 2014

Related U.S. Application Data

(60) Provisional application No. 61/543,917, filed on Oct. 6, 2011.

(51) Int. Cl.
*G01J 3/02* (2006.01)
*G01K 11/32* (2006.01)
*G01N 21/25* (2006.01)
*G02F 1/21* (2006.01)

(52) U.S. Cl.
CPC .............. *G01J 3/0218* (2013.01); *G01K 11/32* (2013.01); *G01N 21/255* (2013.01); *G02F 2001/212* (2013.01)

(58) Field of Classification Search
CPC .......................... G02F 2001/212; G01J 3/0218

USPC ...................................................... 385/12, 13
See application file for complete search history.

(56) References Cited

U.S. PATENT DOCUMENTS 3,823,996 A     7/1974  Kompfner et al.
4,889,986 A *  12/1989  Kersey ............... G01D 5/35383
                                              250/227.19

(Continued)

FOREIGN PATENT DOCUMENTS

EP    0213778 A2    3/1987
JP    H04307328     10/1992

(Continued)

OTHER PUBLICATIONS

Lu, "Tapered Fiber Mach-Zehnder interferometer for simultaneous measurement of refractive index and temperature", Applied Physics Letters 94, Apr. 3, 2009, 131110 [retrieved on Dec. 12, 2012].

(Continued)

*Primary Examiner* — Daniel Petkovsek
(74) *Attorney, Agent, or Firm* — Wendy Koba, Esq.

(57) ABSTRACT

A broadband fiber optic sensor array is formed along a length of single mode optical fiber, with the individual sensing elements formed by introducing local perturbations (e.g., changes in diameter) along the length of the optical fiber. The sensor array requires only a single light source input and a single (conventional) optical spectrum analyzer output and is capable of providing individual measurements (such as local temperature or pressure) for each sensing element disposed along the length of fiber. The individual transmission spectra of the sensing elements forming the array are smooth and strongly overlap, and a method has been developed for determining the characteristics of the individual elements from the variations in the total (combined) transmission spectrum.

9 Claims, 2 Drawing Sheets

(56) References Cited

U.S. PATENT DOCUMENTS

| | | | | |
|---|---|---|---|---|
| 5,157,457 A | * | 10/1992 | Taylor | A61B 5/1459 250/227.19 |
| 5,295,205 A | | 3/1994 | Miller et al. | |
| 5,337,376 A | * | 8/1994 | Ravetti | G01N 21/7703 250/227.14 |
| 5,664,037 A | | 9/1997 | Weidman | |
| 6,226,091 B1 | | 5/2001 | Cryan | |
| 7,514,670 B2 | * | 4/2009 | Anderson | G08B 13/186 250/227.14 |
| 8,368,899 B2 | * | 2/2013 | Sumetsky | G01D 5/35329 356/477 |
| 2002/0157422 A1 | | 10/2002 | Corio et al. | |
| 2003/0180001 A1 | | 9/2003 | Gonthier | |
| 2011/0032529 A1 | | 2/2011 | Wan et al. | |

FOREIGN PATENT DOCUMENTS

| | | |
|---|---|---|
| JP | 2000161910 | 6/2000 |
| JP | 2008157759 | 7/2008 |
| JP | 2009025199 | 2/2009 |
| JP | 4597251 | 12/2010 |

OTHER PUBLICATIONS

Li, "Ultra-Abrupt Tapered Fiber Mach-Zehnder Interferometer Sensors", May 27, 2011, Sensors 2011, pp. 5729-5739 [retrieved on Dec. 12, 2012].

* cited by examiner

US 9,395,242 B2

BROADBAND FIBER SENSOR ARRAY

CROSS-REFERENCE TO RELATED APPLICATIONS

This application claims the benefit of U.S. Provisional Application No. 61/543,917, filed Oct. 6, 2011 and herein incorporated by reference.

TECHNICAL FIELD

The present invention relates to a fiber sensor array and, more particularly to a broadband fiber sensor array based on a plurality of sensing elements formed along a section of optical fiber, with each sensing element including unique perturbations and thus exhibiting a different transmission spectrum, allowing for a plurality of sensing parameter values to be determined from a single measurement of the output transmission spectrum of the fiber sensor array.

BACKGROUND OF THE INVENTION

It is known in the art to form a sensor array by providing an optical fiber with multiple sensing segments separated by weakly reflecting portions, such as fiber Bragg grating reflectors. The sensing segments undergo a change in refractive index in response to changes in a physical condition (such as temperature, pressure, refractive index value), resulting in changes in the transmitted optical signal. An analysis of the transmission spectrum of the output optical signal can then be used to determine these local changes in physical condition along the length of the fiber.

In particular, a fiber sensor array may be used to monitor the characteristics of a medium (e.g., gas or liquid) adjacent to a fiber as well as the fiber itself. The characteristics include, for example, changes in temperature, pressure, refractive index, electromagnetic field, mechanical properties (stress, strain), chemical properties (introduction of a noxious gas into the ambient, for example), etc., where the characteristics are monitored by measuring one or more variations in the properties of light propagating along the optical fiber. Suitable properties to be measured include, but are not limited to, spectrum, polarization, pulse characteristics and the like.

One conventional type of fiber sensor array utilizes a plurality of fiber Bragg gratings (FBGs) formed along disparate sections of an optical fiber. An FBG sensor array monitors shifts of narrow Bragg resonances in response to changes in the environment, where each grating forming the array has a different, narrow resonant wavelength. As a result, a plurality of FBGs with different resonant wavelengths may be disposed in series along a single optical fiber so that all of the individual resonance shifts are separated and can be determined from a single transmission or reflection spectral measurement.

While useful in forming an "array" sensor that requires an analysis of only a single output signal, the need to evaluate several different, narrow resonances along the spectrum requires expensive optical analyzers with the required fine spectral resolution capability. Additionally, FBG sensors have somewhat limited applicability inasmuch as the gratings themselves degrade at relatively high temperatures. In particular, UV-inscribed gratings become unstable at elevated temperatures. Thus, FBG sensor arrays are not suitable for applications where the sensor may be exposed to extreme temperature (or other environmental) conditions.

In contrast, other types of sensors, such as Mach-Zehnder fiber interferometer sensors, are more robust and can be used in high temperature environments, since they do not require include UV-inscribed gratings. A Mach-Zehnder interferometer (MZI) type of sensor does not use resonance wavelength analysis and is considered to be more broadband than an FBG sensor. Advantageously, since there is no need to monitor shifts in narrow wavelength resonances, the MZI sensor does not require the use of expensive optical spectrum analyzers. However, it is difficult to arrange the MZI type of sensor in an array configuration so that a plurality of individual sensors receive a common input signal and their output signals can thereafter be combined and applied as an input to a single optical spectrum analyzer or other type of detector arrangement. Unlike the spectral resonances of the FBG sensor array, the broadband element spectra of an MZI strongly overlap and it is unclear how to separate individual sensor contributions from the spectrum of the entire array.

Therefore, a need remains for a fiber sensor array configuration that retains the robust, broadband attributes of an MZI-based system, yet is able to provide the individual sensor-based results associated with an FBG array system and is also able to operate under high temperature conditions.

SUMMARY OF THE INVENTION

The needs remaining in the prior art are addressed by the present invention, which relates to a fiber sensor array and, more particularly to a broadband fiber sensor array based on a plurality of sensing elements formed along a section of optical fiber, with each sensing element including unique perturbations and thus exhibiting a different transmission spectrum, allowing for a plurality of sensing parameter values (e.g., a plurality of temperatures) to be determined from a single measurement of the output transmission spectrum of the fiber sensor array.

In accordance with the present invention, a fiber sensor array is formed by introducing a plurality of local perturbations along a length of an optical fiber, each local perturbation forming a sensing element Each sensing element functions as an MZI, transforming at least a fraction of the mode of the propagating signal into higher order modes (HOMs) and then back again into the original propagating mode. The optical fiber can be single-moded or multi-moded, and/or may comprise one or more cores, where, in a multicore configuration, at least one core responds differently to the perturbation or sensing parameters when compared to the other core(s). The individual characteristics of the sensors (e.g., temperature and applied stress) associated with the plurality of sensing elements can then be extracted from the final output transmission spectrum such that local values of a characteristic being measured (hereinafter referred to at times as a "sensing parameter") can be calculated (local temperature being one sensing parameter capable of being calculated from the spectra associated with the sensing elements forming the array of the present invention).

Each sensing element may be first calibrated to define its "control" transmission spectrum in the absence of environmental changes (referred to at times as the "calibration spectrum"). Upon being deployed, the output transmission spectrum from the sensor array is analyzed in conjunction with the plurality of calibration spectra to determine the "local" values of a selected sensing parameter. In particular, for a plurality of N sensing elements, the value of the output transmission spectrum at N separate wavelengths can be used to determine the local value of the sensing parameter at each of the plurality of N sensing elements. While it is necessary to use measurements at N separate wavelengths, the use of more than N wavelengths has been found to improve the accuracy of the results.

In accordance with the present invention, the local perturbations may take the form of local variations in the diameter, the refractive index profile, or index properties of the optical fiber, local variations in the doping levels in the core and/or cladding, local variations in the "type" of optical fiber (e.g., standard single mode fiber, photonic crystal fiber, large mode area fiber, etc.), local variations in the physical length or effective optical length of a specific perturbation, or any combination thereof.

It is to be additionally understood that various types of single mode fiber may be used to form the sensing elements of the fiber sensor array. In situations where high temperature measurements may be required, it is considered preferable to use a pure silica fiber, such as a photonic crystal fiber, which is not as susceptible to degradation in performing in the presence of high temperatures as standard (doped) optical fiber.

It is an aspect of the present invention that the functions are all linearly independent so that the local values of the sensing parameter can be determined from a set of N measurements for N sensing elements.

It is another aspect of the present invention that the fiber sensor array can be used to determine the value of M different sensing parameters (temperature, pressure, change in refractive index, etc.) at each sensing element, by using measurements from at least M*N different wavelengths.

Other and further aspects of the present invention will become apparent during the course of the following discussion and by reference to the accompanying drawings.

BRIEF DESCRIPTION OF THE DRAWINGS

Referring now to the drawings, where like numerals represent like parts in several views.

DETAILED DESCRIPTION

The present invention, as described in detail below, discloses a broadband fiber optic sensor array that is formed along a length of optical fiber. The sensor array requires only a single light source input and a single (conventional) optical spectrum analyzer output and is capable of providing individual measurements for each sensing element disposed along the length of fiber. The individual transmission spectra of the sensing elements forming the array are smooth and may strongly overlap, and a method has been developed for determining the characteristics of the individual elements from the variations in the total (combined) transmission spectrum.

Figure 1:
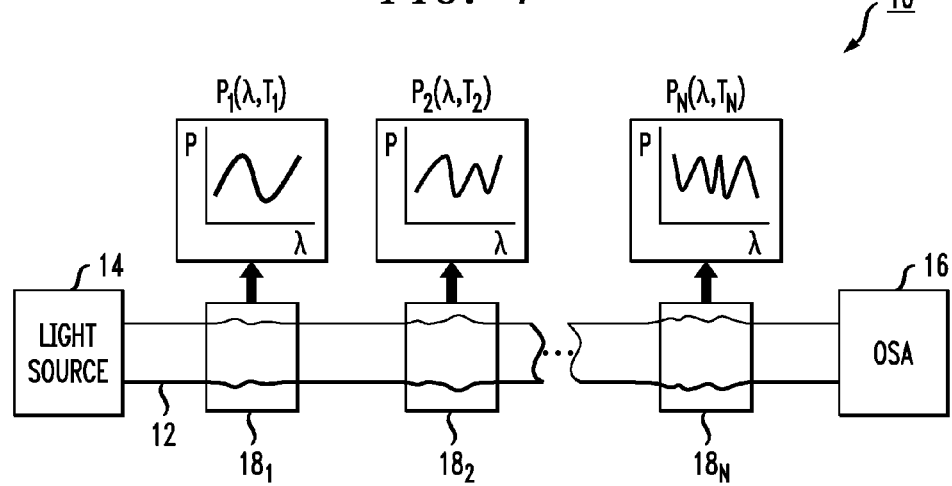
FIG. 1 illustrates an exemplary broadband fiber sensor array formed in accordance with the present invention.

FIG. 1 illustrates an exemplary broadband fiber sensor array 10 formed in accordance with the present invention. As shown broadband fiber sensor array 10 comprises a single mode optical fiber 12 responsive to an input optical signal from a light source 14. The output from optical fiber 12 is thereafter directed into an optical spectrum analyzer (OSA) 16 which measures the transmission spectrum at the output of optical fiber 12. The transmission spectrum may be determined using any of several well-known methods. For example, the optical signal should have a bandwidth large enough to interrogate a sufficient portion of the spectral extent of the response of the sensor array, thus forming a signal with the desired accuracy. In another example, the source could exhibit a narrow bandwidth, but be tunable across the desired spectral range. In this case, the measurement may be performed with a power meter.

In accordance with the present invention, a plurality of N separate sensing elements 18 are disposed along optical fiber 12, shown as sensing elements $18_1, 18_2, \ldots, 18_N$ in FIG. 1. Each sensing element $18_i$ is formed by incorporating local perturbations in optical fiber 12 such that each element exhibits a different, unique transmission spectrum. The local perturbations can take the form of, for example, variations/perturbations in the local diameter of the fiber, variations in the refractive index profile or index properties (which may arise from variations in dopant distributions in the core and/or cladding or through modification of the strain state of the fiber), concatenating different types of fiber, or any combination of these or other types of perturbations that will alter the modal properties of the propagating signal.

Each sensing element 18 functions as an MZI, which transforms at least a fraction of one mode, such as the fundamental mode, of the signal propagating along optical fiber 12 into one or more higher order modes, and then back to the original mode again. The transmission power spectra $P_i(\lambda, T_n)$ of each sensing element $18_i$ is also shown in FIG. 1, where it is obvious that each is unique in terms of transmitted power as a function of wavelength. The transmission power spectra depend on both wavelength $\lambda$ and the specific sensing parameter $T_n$ (i.e., the 'characteristic' being measured/sensed, such as temperature, pressure, refractive index, etc.). These spectra result from the interference between the original signal mode and higher order modes as the optical signal propagates through each separate sensing element $18_i$.

It is assumed that inasmuch as the higher order modes exhibit a relatively higher propagating loss, these modes will attenuate before reaching the next sensing element in the array. Preferably, they will attenuate to a level that will not influence the spectral characteristics of downstream sensing element. As an option, the broadband fiber sensor array of the present invention can be configured such that the local perturbations are relatively small, ensuring that any energy remaining in higher order modes from a previous sensing element can be ignored. It is possible that the higher order modes may not significantly attenuate and, in that case the effects of their interference and reflections can be taken into account by calibration and/or numerical modeling, which can be used for determination of the parameters of the individual sensor elements. In some cases, it is desirable that the perturbations are not large enough to introduce reflections of the light along the signal path.

To determine multiple sensing parameters at a local position, multiple fibers or one fiber with multiple cores with different responses to the sensing parameter can be used. For example, if the fiber contains two cores each having a different waveguide design or composition (which cause the cores to respond differently to sensing parameters such as temperature and strain), a taper in fiber diameter will cause the cores to exhibit different transmission spectra, allowing for separation of the effects of temperature and strain.

In accordance with the present invention, it is presumed that for any sensing parameter, such as temperature T, all functions $P(\lambda, T)$ are linearly independent. This is an important aspect of the present invention, and allows for the individual sensing parameter values to be recovered by an analysis of the single output transmission spectrum from each core of the sensor array. Therefore, since each sensing element is linearly independent, the total transmission power through broadband fiber sensor array 10, denoted as $P_{tot}(\lambda, T_1, T_2, \ldots, T_N)$, is found as a product of the partial transmission powers at the individual sensing elements:

$$P_{tot}(\lambda, T_1, T_2, \ldots, T_N) = \Pi_{n=1}^{N} P_n(\lambda, T_n).$$

Expressing this relation in the logarithmic scale then provides a sum of the contributions from the individual sensing elements, or:

$$\log(P_{tot}(\lambda, T_1, T_2, \ldots, T_N)) = \Sigma_{n=1}^{N} \log(P_n(\lambda, T_n)). \quad (1)$$

Using this relation, the local sensing parameters $T_n$ can then be determined from the total power $P_{tot}$ once each sensing element $18_i$ has been initially calibrated to define its local transmission spectrum (referred to at times as its calibration spectrum C). That is, once all "local" power spectra $P_n$ are created from an initial calibration process, the individual local parameters $T_n$ can be restored from the single spectrum $\log(P_{tot}(\lambda, T_1, T_2, \ldots, T_N))$, using a set of measurements from at least N different values of wavelength $\lambda$ (i.e., creating a system of N equations with N unknowns). It is to be understood that there are several cases where calibration may not be necessary, such as, for example, when only relative changes in a parameter are to be determined.

Figure 2:
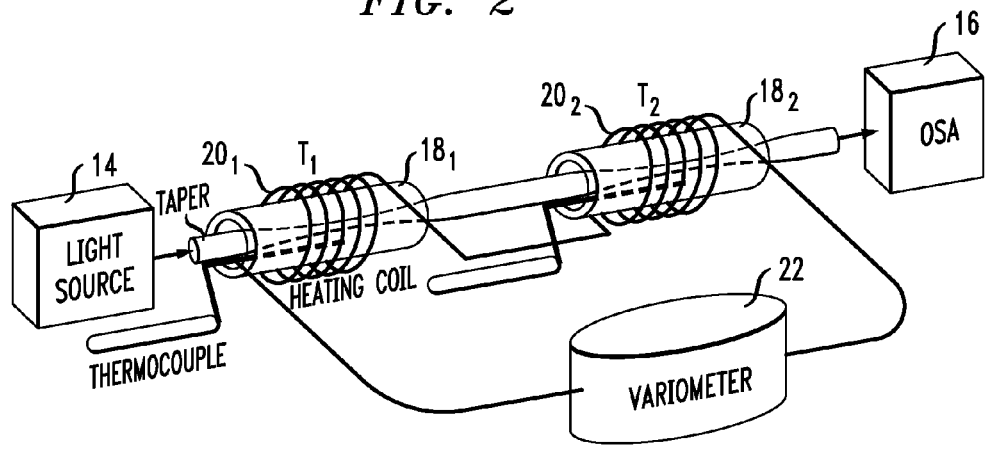
FIG. 2 shows a particular two-element broadband fiber sensor array of the present invention, as configured to first determine the calibration characteristics of each sensing element.

An arrangement for performing an initial calibration is shown in FIG. 2, in this case for a broadband fiber sensor array 10 including a pair of sensing elements $18_1$ and $18_2$. In this particular arrangement, a "perturbation" in the form of a biconical taper is utilized to form each sensing element. The tapers are formed to have different lengths and, therefore, their transmission spectra $\log(P_1(\lambda, T_1))$ and $\log(P_2(\lambda, T_2))$ will be unique and linearly independent. The local characteristic (i.e., "sensing parameter") being analyzed in this arrangement is the temperature and the calibration equipment takes the form of a pair heating coils $20_1$ and $20_2$ disposed to surround biconical taper sensing elements $18_1$ and $18_2$, respectively. A variable transformer (i.e., variometer) 22 is used to separately control/change the temperature of each heating coil 20. A pair of thermocouples $24_1$ and $24_2$ is associated respectively with sensing elements $18_1$ and $18_2$ to record the "local" temperature values during the calibration process, where these recorded values will later be used to compare the theoretical results of using the sensor array of the present invention with direct, individual measurements.

Figure 3:
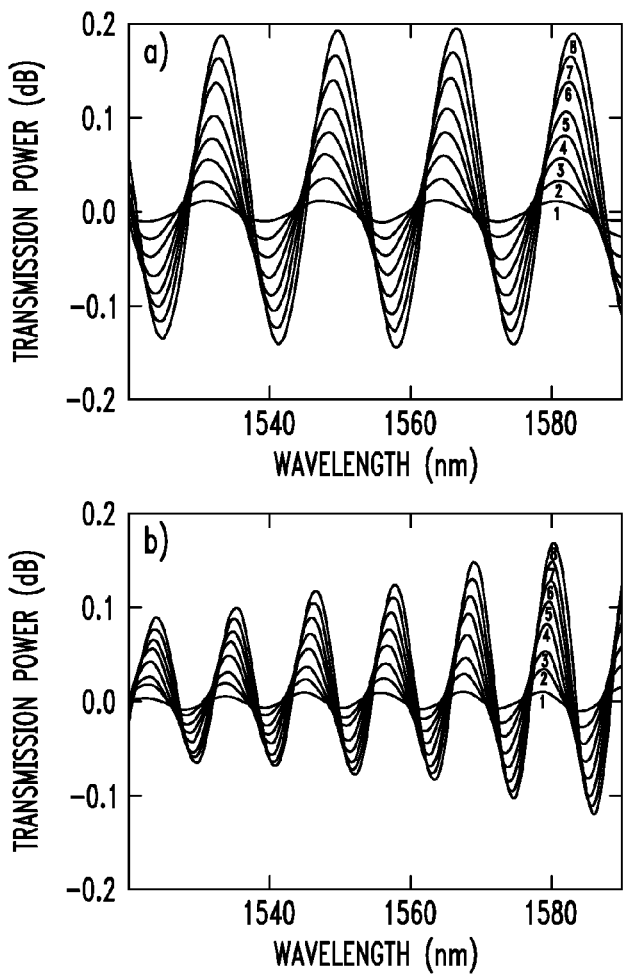
FIG. 3 contain graphs of the calibration output from both the first sensing element and the second sensing element in the arrangement of FIG. 2, FIG. 3(a) associated with the first sensing element and FIG. 3(b) associated with the second sensing element.

In one example of performing the calibration process, the local temperature of one sensing element was held constant (at room temperature, 22° C.), and the local temperature of the other sensing element was increased from room temperature in steps of 50° C., up to a temperature of 400° C. FIG. 3(a) shows the results of the calibration process for sensing element $18_1$, that is a set of plots of spectral variations as a function of temperature defined as follows:

$$C_{18_1}(\lambda, T^{(k)}) = 10 \log(P_{tot}(\lambda, T^{(k)}, T^{(0)})) - 10 \log(P_{tot}(\lambda, T^{(0)}, T^{(0)})),$$

where $T^{(0)} = 22°$ C. and $T^{(1)} - T^{(k+1)} = 50°$ C., $k=1, 2, \ldots 8$. FIG. 3(b) shows the calibration results for sensing element $18_2$, where it is clear that the two power spectra are different, based upon the differences in the physical design of the biconical fiber tapers.

Figure 4:
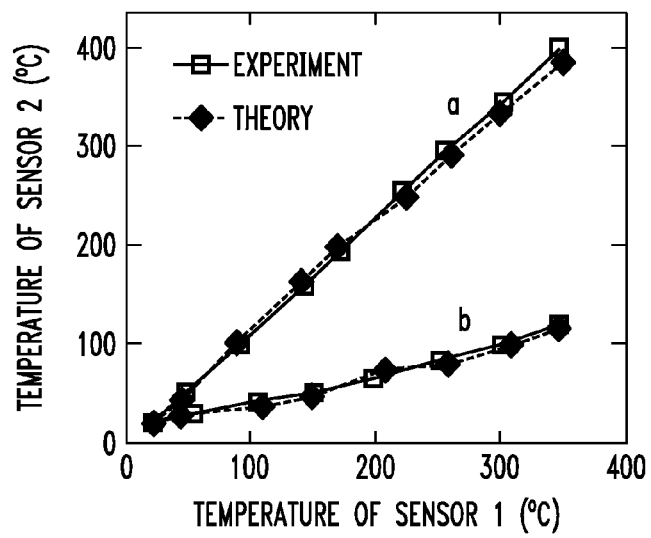
FIG. 4 is a graph comparing the results of direct measurement of ambient temperature changes with utilizing the output from a broadband fiber sensor array of the present invention.

Once the calibration spectra are obtained, local temperatures T at each sensing element can be determined by performing a single measurement of the output transmission spectrum from the sensor array, and evaluating the result at each different wavelength (for example, using two sensing elements would determine two temperature values $T_1$ and $T_2$). FIG. 4 contains plots comparing the "computed" values of $T_1$, $T_2$ determined using the process of the present invention with "actual" values measured with a pair of thermocouples, as shown in FIG. 2.

In a first experiment (shown as plots a in FIG. 4), heating coils $20_1$ and $20_2$ were equally configured, providing essentially the same temperature to each of the sensing elements $18_1$ and $18_2$. In the second experiment, different temperatures were applied to the pair of sensing elements, yielding the results as shown in plots b. In both cases, the theoretically predicted values (calculated using the relations of the present invention) are shown to be in agreement with the actual values measured by the thermocouples.

In accordance with equation (1) as defined above, the theoretical plots as shown in FIG. 4 were determined by extrapolating the calibration spectra $C_P(\lambda, T^{(k)})$ from discrete to continuous temperature values. According to this relation, the variation of the experimentally measured transmission spectrum can be defined as follows:

$$C_{ot}(\lambda, T_1, T_2) = 10 \log(P_{tot}(\lambda, T_1, T_2)) - 10 \log(P_{tot}(\lambda, T^{(0)}, T^{(0)})) = C_1(\lambda, T_1) + C_2(\lambda, T_2) \quad (2).$$

In the above, the relation $C_{ot}(\lambda, T_1, T_2)$ is known from the experiment, and the functions $C_1(\lambda, T_1)$ and $C_2(\lambda, T_2)$ are known from calibration and extrapolation. Within measurement errors, equation (2) is valid for all wavelengths $\lambda$, even though only two separate wavelengths $\lambda_1$ and $\lambda_2$ are "mathematically" required to determine the values of $T_1$ and $T_2$. However, for better accuracy, additional wavelengths can be used, and in associated numerical simulations, the equation is solved by minimizing the following:

$$\Sigma_\lambda |C_{tot}(\lambda, T_1, T_2) - C_1(\lambda, T_1) - C_2(\lambda, T_2)|^2,$$

for multiple values of $\lambda$.

While the above description of the principles of the present invention have been associated with determining the local temperature of each sensing element, it is to be understood that this is exemplary only, and various other physical parameters (pressure, refractive index, acoustic, etc.), may similarly be determined, once a set of calibration functions are determined. Indeed, it is another aspect of the present invention that the same premise may be used to determine a plurality of separate physical parameters associated with each of the sensing elements, presuming that each parameter is linearly independent from the other values. In general terms, therefore, a plurality of M physical parameters may be determined for a set of N sensing elements, based upon a single measurement of the transmission spectrum. In order to achieve this result, an M×N array of calibration functions must first be determined for the sensor array. Once this calibration matrix is created, the process of finding the individual parameter values proceeds as outlined above.

Moreover, while various types of optical fiber, both single mode and multimode, are suitable for use in the broadband fiber sensor array of the present invention, pure silica single mode photonic crystal fiber (PCF) is a preferred choice for high temperature applications, where the silica material forming the PCF remains essentially unaffected by temperature extremes.

While a preferred embodiment of the present invention has been set forth, those skilled in the art who have reviewed this disclosure will appreciate that modifications can be made within the scope of the invention. Therefore, the present invention should be construed as limited only by the claims as appended hereto.

What is claimed is:

1. A broadband fiber sensor array formed along a length of optical fiber, said sensor array for measuring at least one sensing parameter at a plurality of separate locations along the length of optical fiber and comprising:
    an input optical signal source coupled to a first end termination of the optical fiber for supplying an optical input signal to the broadband fiber sensor array;
    an optical detector coupled to the output of the single mode fiber for measuring the output transmission spectrum; and
    a plurality of N sensing elements formed along the length of the optical fiber for measuring a plurality of N local values of the at least one sensing parameter, each sensing element including local perturbations created in the optical fiber to form a local Mach-Zehnder interferometer (MZI) therein, the local perturbations being different in each sensing element such that a plurality of initial calibration spectra associated with the plurality of N sensing elements are linearly independent, where the plurality of local values of the at least one sensing parameter are determined from a comparison of the output transmission spectrum of the broadband fiber sensor array to the plurality of N initial calibration spectra.

2. A broadband fiber sensor array as defined in claim 1 wherein the optical detector comprises an optical spectrum analyzer.

3. A broadband fiber sensor array as defined in claim 1 wherein the optical detector comprises an optical power meter.

4. A broadband fiber sensor array as defined in claim 1 wherein the local perturbation comprises a local perturbation in the diameter of the optical fiber.

5. A broadband fiber sensor as defined in claim 1 wherein the local perturbation is selected from the group consisting of: optical fiber diameter, doping index profile of a core region of the optical fiber, doping index profile in a cladding region of the optical fiber, type of optical fiber, and any combination thereof.

6. A broadband fiber sensor array as defined in claim 1 wherein the at least one sensing parameter is selected from the group consisting of: temperature, pressure, refractive index, mechanical properties and chemical properties.

7. A broadband fiber sensor array as defined in claim 1 wherein a plurality of M sensing parameters are measured at each sensing element, with an initial calibration spectrum created for each sensing parameter at each sensing element of the plurality of N sensing elements and the plurality of M sensing parameters are measured for each sensing element using an M×N calibration matrix.

8. A broadband fiber sensor array as defined in claim 1 wherein the optical fiber comprises a single mode optical fiber.

9. A broadband fiber sensor array as defined in claim 1 wherein the optical fiber comprises a multicore optical fiber, where each core comprises different properties and responds differently to the local perturbations.

* * * * *